US007640804B2

(12) United States Patent
Daumer et al.

(10) Patent No.: US 7,640,804 B2
(45) Date of Patent: Jan. 5, 2010

(54) APPARATUS FOR MEASURING ACTIVITY

(75) Inventors: Martin Daumer, Munich (DE); Michael Scholz, Munich (DE)

(73) Assignee: Trium Analysis Online GmbH, Munich (DE)

( * ) Notice: Subject to any disclaimer, the term of this patent is extended or adjusted under 35 U.S.C. 154(b) by 344 days.

(21) Appl. No.: 11/412,068

(22) Filed: Apr. 27, 2006

(65) Prior Publication Data

US 2006/0288781 A1 Dec. 28, 2006

(30) Foreign Application Priority Data

Apr. 27, 2005 (DE) .................. 10 2005 019 924

(51) Int. Cl.
G01P 3/04 (2006.01)
(52) U.S. Cl. .............. 73/510; 73/513; 73/527; 73/530
(58) Field of Classification Search .......... 73/510, 73/489, 513, 527, 530; 600/595
See application file for complete search history.

(56) References Cited

U.S. PATENT DOCUMENTS

| | | | | |
|---|---|---|---|---|
| 4,112,926 A | * | 9/1978 | Schulman et al. | 600/595 |
| 4,566,461 A | * | 1/1986 | Lubell et al. | 600/481 |
| 5,263,491 A | * | 11/1993 | Thornton | 600/587 |
| 5,314,389 A | * | 5/1994 | Dotan | 482/3 |
| 5,485,402 A | * | 1/1996 | Smith et al. | 702/160 |
| 5,657,514 A | * | 8/1997 | Fabrizio | 24/265 BC |
| 5,891,042 A | * | 4/1999 | Sham et al. | 600/483 |
| 5,941,836 A | * | 8/1999 | Friedman | 600/595 |
| 6,129,686 A | * | 10/2000 | Friedman | 600/595 |
| 6,506,152 B1 | * | 1/2003 | Lackey et al. | 600/300 |
| 7,062,225 B2 | * | 6/2006 | White | 455/41.2 |
| 2003/0065257 A1 | * | 4/2003 | Mault et al. | 600/407 |
| 2003/0208113 A1 | * | 11/2003 | Mault et al. | 600/316 |
| 2006/0189924 A1 | * | 8/2006 | Blakley et al. | 604/66 |

(Continued)

OTHER PUBLICATIONS

Kurtzke JF., Rating neurologic impairment in multiple sclerosis: An expanded disabilit status scale (EDSS). Neurology, 1983, 33: 1444-1452.

(Continued)

Primary Examiner—Hezron Williams
Assistant Examiner—Samir M Shah
(74) Attorney, Agent, or Firm—Edell, Shapiro & Finnan, LLC

(57) ABSTRACT

An activity measuring device (1) is used for recording the activity of a test subject, where the device (1) is attachable so as to be carried on the body of the test subject. According to the invention it is planned that the activity measuring device is located on a buckle (2) of a belt (3) which can be fitted to the body of the test subject, and that it has acceleration sensors (10, 10') for detection of acceleration in all three spatial directions at right angles to each other. Furthermore, the activity measuring device (1) telemeters the recorded measurement data via a radio link to a central server (7), by virtue of the fact that the measurement data recorded by the activity measuring device (1) can be transmitted by means of a connecting cable (5) to a mobile telephone (4) via a device interface of the mobile telephone (4), which is arranged so as to be carried on the belt, and can be sent from there to the external server (7) via a radio link.

20 Claims, 2 Drawing Sheets

U.S. PATENT DOCUMENTS

2007/0208233 A1* 9/2007 Kovacs ..................... 600/300
2008/0001735 A1* 1/2008 Tran ....................... 340/539.22
2008/0167573 A1* 7/2008 Stivoric et al. ............. 600/549
2008/0281234 A1* 11/2008 Goris et al. ................ 600/595

OTHER PUBLICATIONS

Albrecht H, Wötzel C, Erasmus LP, Kleinpeter M, König N, Pöllmann W., Day-to-day variability of maximum walking distance in MS patients can mislead to relevant changes in the Expanded Disability Status Scale (EDSS): average walking speed is a more constant parameter. Mult. Scler., 2001, 7: 105-9.

Goodkin DE., EDSS reliability. Neurology, 1991, 41:331-332.

Kesselring J, Beer S., Symptomatic therapy and neurorehabilitation in multiple sclerosis. Lancet Neurology, Oct. 2005, 4(10): 643-52.

Motl RW, McAuley E, Snook EM, Scott JA., Accuracy of two electronic pedometers for measuring steps taken under controlled conditions among ambulatory individuals with multiple sclerosis. Mult. Scler., 2005, 11: 343-345.

Busse ME, Pearson OR, Van Deursen R, Wiles CM., Quantified meaurement of activity provides insight into motor function and recovery in neurological disease. J Neurol Neurosurg Psychiatry, 2004, 75: 884-888.

Bussmann JBJ et al., Ambulatory Monitoring of Mobility-Related Activities: the Initial Phase of the Development of an Activity Monitor. Eur. J. Phys. Med. Rehabil., 1995, 5(1): 2-7.

Randell C, Muller H., The Well Mannered Wearable Computer. Pers. and Ubiq. Comp., 6(1): 31-36.

Jovanov E, Milenkovic A, Otto C, De Groen P., A wireless body area network of intelligent motion sensors for computer assisted physical rehabilitation. J. of NeuroEng. and Rehab., 2005, 2:6.

Daumer M, Neiβ A., A new adaptive algorithm to detect shifts, drifts and outliers in biodmedical time series. Math. Stat. with Appl. in Biometry, Josef Eul Verlag, Cologne, 2001, 265-275.

Srinivasan M, Ruina A., Computer optimization of a minimal biped model discovers walking and running. Nature, 439: 72-75.

Grillner S., Neural Networks for Verterbrate Locomotion. Scientific American, Jan. 1996, 274(1): 64-9.

Perry J., Gait analysis—normal and pathological function. Slack Incorporated 1992, New Jersey, Chapter 1 and 2.

Ioannidis JPA., Why Most Published Research Findings Are False. PLoS Med, 2(8): e124.

Bussmann JBJ, Van De Laar YM, Neelemann MP, Stam HJ., Ambulatory accelerometry to quantify motor behaviour in patients after failed back surgery: a validation study. Pain, 1998, 74: 153-161.

Brown G., An Accelerometer Based Fall Detector: Development, Experimentation, and Analysis. Summer Undergraduate Program in Engineering at Berkeley (SUPERB), Jul. 2005.

Cho SY, Park CG, Jee GI., Measurement System of Walking Distance Using Low-cost Accelerometers. TM8-6, The 4th Asian Control Conference, Singapore, 2002, 1799-1803.

Foerster F, Smeja M, Fahrenberg J., Detection of posture and motion by accelerometry: a validation study in ambulytory monitoring. Computers in Behaviour, 1999, 15: 571-583.

Walker DJ, Heslop PS, Plummer CJ, Essex T, Chandler S., A continuous patient activity monitor: validation and relation to disability. Pysiol. Meas., United Kingdom, 1197, 18: 49-59.

Mayagoita RE, Waarsing JH, Sanchez-Pineda A, Veltink PH., Walking balance study using a triaxial accelerometer. Poster presented at Measuring Behaviour '98, 2nd Internantional Conference on Methods and Techniques in Behavioral Research, Aug. 1998, Groningen, The Netherlands.

King GA, Torres N, Potter C, Brooks TJ, Coleman KJ., Comparison of Activity Monitors to Estimate Energy Cost of Treadmill Exercise. Medicine & Science in Sports & Excercise, 2004, 1244-1251.

Levine JA, Baukol PA, Westerterp KR., Validation of the Tracmor triaxial accelerometer system for walking. Medicine & Science in Sports & Excercise, 2001, 1593-1597.

Lyons GM, Culhane KM, Hilton D, Grace PA, Lyons D., A description of an accelerometer-based mobility monitoring technique. Medical Engineering & Physics, 2005, 27: 497-504.

Powell SM, Rowlands AV., Intermonitor Variabiliity of the RT3 Accelerometer during Typical Physical Activities. Medicine & Science in Sport & Excercise, Feb. 2004, 36(2): 324-330.

Steele BG, Holt L, Belza B, Ferris S, Lakshminaryan S, Buchner DM., Quantitating Physical Activity in COPD Using a Triaxial Accelerometer. CHEST The Cardiopulmonary and critical care journal, 2000, 117: 1359-1367.

Iltis PW, Givens MW., Validation Of The CALTRACTM Accelerometer During Simulated Mult-Geared Cycling At Different Work Rates. JEPonline Journal of Exercise Physiology online, Apr. 2000, vol. 3 No. 2: 22-27.

Veltink PH, Bussmann HBJ, De Vries W, Martens WLJ, Van Lummel RC., Detection of Static and Dynamic Activities Using Uniaxial Acclerometers. IEEE Transactions on Rehabilitation Engineering, Dec. 1996, vol. 4 No. 4: 375-385.

* cited by examiner

APPARATUS FOR MEASURING ACTIVITY

FIELD OF THE INVENTION

The invention relates to an activity measuring device for recording the activity of a test subject and furthermore a method for recording the activity of a test subject.

BACKGROUND

Such devices, which are attachable to the body of a test subject, are for example known as so-called pedometers; during the running or walking motion of the test subject, acceleration forces arising on the body are recorded via an acceleration sensor of the pedometer attached to the body and the number of steps completed is counted. The number of steps so determined is a measure of the physical activity of the test subject. Such pedometers are used for sport or fun and have only a unidimensional accelerator sensor for recording accelerations in a vertical direction.

Such a device, however, can only be used to a limited extent in the field of clinical medicine for determination of the degree of physical disability of patients, in particular of patients suffering from multiple sclerosis (hereinafter abbreviated to MS patients), since with this state of the art only dynamic types of motion, such as walking and jogging, can be recorded in an undifferentiated way, while in the case of MS patients with a more severe degree of disability continuous walking or jogging is only possible to a limited extent, or not possible at all, and the types of motion are limited to static states such as lying, sitting and standing, as can be seen from Table 1 below, which shows the so-called "Hauser Ambulation Index" for medical classification of multiple sclerosis patients, with the scale of this index extending from Level 0 to 9. Low values correspond to no or only slight disability, whereas high values correspond to a greater degree of disability.

TABLE 1

| | |
|---|---|
| 0 | No symptoms, fully active |
| 1 | Normal walking behaviour, but the patient reports disability in sports and other demanding activities |
| 2 | Unusual gait or occasionally disturbed equilibrium; the unusual gait is noticed by relatives and friends, takes not more than 10 s for 8 m |
| 3 | Can walk unaided, takes not more than 20 s for 8 m |
| 4 | Needs support on one side (crutch or stick), takes not more than 20 s for 8 m |
| 5 | Needs support on both sides (crutches, sticks or walking aid) and takes more than 20 s for 8 m |
| 6 | Needs support on both sides and takes more than 20 s for 8 m, can sometimes use a wheelchair |
| 7 | Walking is limited to a few steps with support on both sides, can no longer walk 8 m, can use the wheelchair for most activities |
| 8 | Confined to the wheelchair, can still move it him/herself |
| 9 | Confined to the wheelchair, can no longer move it him/herself |

Apart from the "Hauser Ambulation Index" summarized in Table 1, there are also other measurement systems for grading or classification of the degree of disability of MS patients. The EDSS (Expanded Disability Status Scale) can be cited here merely as an example. The existence of several such independent classification systems already shows the weaknesses of such a classification, which are due to subjectivity.

At the present time, admission as an inpatient of the attending physician is required in order to continuously monitor whether and to what extent a treatment prescribed for an MS patient is leading to an improvement or a deterioration in the state of health. During each of these regular periods of admission as an inpatient a medical examination is carried out and on this basis a degree of disability is assigned to the patient, the result of the examination being naturally dependent on the momentary state of mind of the patient and also of the examining physician (being in particular also influenced by the so-called "doctor in a white coat" effect) and thus not dependent on objectivizable criteria. The assessment of the efficacy of medication used in MS therapy is therefore not subject to objectivizable criteria, with the consequence that the direction of therapy followed cannot be corrected early enough.

The examination and classification of the degree of disability or of the activity of patients are of particular importance in the development of drugs and in clinical studies to check their efficacy. Naturally, in the course of medication with a drug to be tested, the degree of physical disability is checked at particular intervals. Because of the above-mentioned range of variation in the measurement results obtained in this process, a proper assessment of efficacy is almost impossible at the present time.

SUMMARY

It is therefore the object of the invention to create an activity measuring device and a method with which, in particular for determination of the degree of disability of MS patients, static states such as lying, sitting and standing can be recorded by objectivizable criteria, in addition to the dynamic forms of motion such as walking and jogging or running, and with which corresponding degrees of activity of the patient to be examined can be determined.

In respect of the device the object is achieved by virtue of the facts that the activity measuring device is located on and/or in the buckle of a belt which can be fitted to the body of the test subject, and that it has acceleration sensors for detection of acceleration in all three spatial directions at right angles to each other. Depending on the configuration of the belt buckle, the activity measuring device can be arranged or configured on the buckle (at the front, at the back, on the top, on the bottom or at the side). The activity measuring device can also preferably be arranged in the buckle, if the circuit elements are suitably miniaturized (e.g. as ASIC). A configuration or integration of the activity measuring device in the buckle is then preferred.

As a result of the configuration of the activity measuring device in the belt buckle there is first of all a practical possibility of simple attachment of the device to a test subject. In the case of repairs the belt can simply be taken off or the belt buckle can merely be removed and sent in for repair or maintenance. Furthermore it is also advantageous that it is not regularly necessary to wash the telemetry device configured as a belt. In addition, the arrangement on or in the belt buckle is also advantageous in the sense that as a result of this arrangement the very frequent movements of the extremities (e.g. arms, legs or head), which are not characteristic for an objective determination of the degree of disability of an MS patient, are measured as little as possible, or are suppressed, or only slightly impair the measurement. It is also advantageous that the belt buckle, when the belt is worn as directed, is close to the patient's centre of gravity. By virtue of the orientation of the belt buckle (facing forwards and centred) when the belt is worn as directed, it also becomes possible computationally to record and process the accelerations recorded by the acceleration sensors in a simple manner. The tripod of the spatial directions sensed by the acceleration sensors is then preferably such that one of the spatial directions is perpendicular to the buckle, i.e. in a forward direction when the patient is walking, jogging or running (straight ahead). A further spatial direction is preferably parallel to the vertical.

With particular advantage, different forms of motion, which naturally differ from each other by virtue of characteristic motion sequences with correspondingly acting acceleration forces, can be identified with the activity measuring device according to the invention by the tridimensional recording of acceleration forces occurring on the body. Since the various forms of motion have different energy requirements and thus different degrees of activity, a differentiated assessment of the physical activity of the patient is possible with the device according to the invention and thus provides the physician responsible for treatment with a means of assessing the progress and success of the treatment on the basis of objectivizable criteria, irrespective of a possible variation in the patient's form on the day. Any negative treatment pattern in the case of MS patients, as a result of the administration of inappropriate drugs for example, can thus be already recognized at an early stage on the basis of corresponding measurement results, so that the use of a drug having a negative effect can be promptly stopped again, with the possibility of reducing risks to the patient and keeping costs due to expensive but inappropriate medication under control.

A preferred embodiment of the activity measuring device according to the invention, for optimal recording of the acceleration forces occurring in the different forms of motion, consists in the fact that the activity measuring device located in the belt buckle is configured in such a way that it is attachable close to the center of gravity of the test subject's body.

According to an advantageous embodiment of the invention, the activity measuring device telemeters the recorded measurement data via a radio link to a central server, which is preferably in an external data-protected service center or in the medical treatment center, so that the telemetered data can be directly seen and assessed there by the medical staff. As a result, in judging the patient's physical condition, the attending physician is no longer exclusively dependent on the examinations carried out during the periods of admission as an inpatient, provided that the device according to the invention is also used as directed in the patient's daily routine.

To this end the activity measuring device can be connected electrically to a mobile telephone, which is also attachable so as to be carried on the belt, and which according to a preferred embodiment of the invention is configured as a PDA, in such a way that data transmission can be established between the activity measuring device and the mobile telephone, with the activity measuring device having an electrical connection cable which can be connected electrically to a device interface of the mobile telephone. The connection cable can then provide both for data transmission between the device and the mobile telephone and also, by tapping the battery cells in the mobile telephone, for the power supply of the device. The measurement data recorded by the activity measuring device can be transmitted to the mobile telephone via the device interface of the mobile telephone and can be sent from there to the external server via a GPRS or UMTS radio link, for example.

In an embodiment of the activity measuring device according to the invention which is favorable from the point of view of measurement technology, the acceleration sensors of the activity measuring device are a unidimensionally operating acceleration sensor, for recording acceleration forces acting along the vertical spatial direction, and a bidimensionally operating acceleration sensor, for recording acceleration forces acting at right angles thereto.

An expedient further development of the invention consists in the fact that a section of the belt adjoining the belt buckle on the cable side has a Velcro fastening to receive the connection cable, so that accidental detachment or loosening of the connection cable can be largely prevented and the security of data transmission is thus increased. Furthermore, a microprocessor is provided in the activity measuring device, both for controlling the recording of measurement data and for data transmission. By means of a control program implemented in the microprocessor, the activity measuring device records and transmits the measurement data with a sampling frequency in an order of magnitude of 100 Hz. This sampling frequency has proved to be particularly suitable for resolving even rapid motion sequences of the order of magnitude of a hundredth of a second. The system according to the invention comprises the activity measuring device, the belt, the mobile telephone and preferably also the server.

In respect of the method the object is achieved by virtue of the fact that, in all three spatial directions at right angles to each other, body accelerations underlying the momentary physical activity of the test subject to be examined are continuously measured and a current state of motion is determined therefrom.

To this end, in order to determine the current state of motion of the test subject, a distinction is first made between static and dynamic states of motion, with a distinction being made between sitting, standing and lying in the case of the static states of motion, and between walking and jogging in the case of the dynamic states of motion. In order to distinguish between static and dynamic states of motion, the maximum and minimum in a series of consecutively measured acceleration values determined in the direction of one spatial axis are calculated and the difference between the maximum and the minimum is compared with a threshold value. Maximum and minimum here means a suitable maximum value or minimum value in the series of measurements, as the case may be. In order to prevent any falsification by outliers, for example, a mean from a predetermined number (e.g. ten) of maxima in the series of measurements can be used as the maximum. If then fewer maxima than the predetermined number occur, correspondingly fewer maxima are used for determination of the mean. Correspondingly, a mean from a predetermined number (e.g. ten) of minima in the series of measurements can be used as the minimum. If then fewer minima than the predetermined number occur, correspondingly fewer minima are used for determination of the mean. A movement of the patient is then detected if the inequality max−min>δ is fulfilled in at least one spatial axis direction, where max and min is the maximum value and minimum value, respectively, from a series of consecutively measured acceleration values determined in this spatial axis direction, and δ is a threshold value.

If a movement is detected, in order to distinguish the states of motion walking and jogging, the mean difference from the mean of the measured values in a series of measurements is determined for each spatial axis direction and the difference so determined from the mean in the corresponding spatial axis direction is compared with a threshold value assigned in each case. In order to distinguish the states of motion lying, standing and sitting for each spatial axis direction, on the other hand, the mean of the corresponding series of measurements is determined and the means determined in each case are compared with assigned threshold values. A corresponding degree of activity can be determined by ascertaining the duration and, where appropriate, step frequency for each form of motion identified.

The invention, as well as further features, aims, advantages and possible applications thereof, is/are explained in greater detail below on the basis of a description of preferred embodiments, with reference to the appended drawings. In the drawings the same or similar reference marks designate the same or corresponding elements, as the case may be. All the features that are described and/or graphically represented, by themselves or in any desired meaningful combination, constitute the object of the present invention, irrespective of the summary thereof in the claims or their back reference. The following are shown in the drawings in highly schematic form:

DETAILED DESCRIPTION

Figure 1:
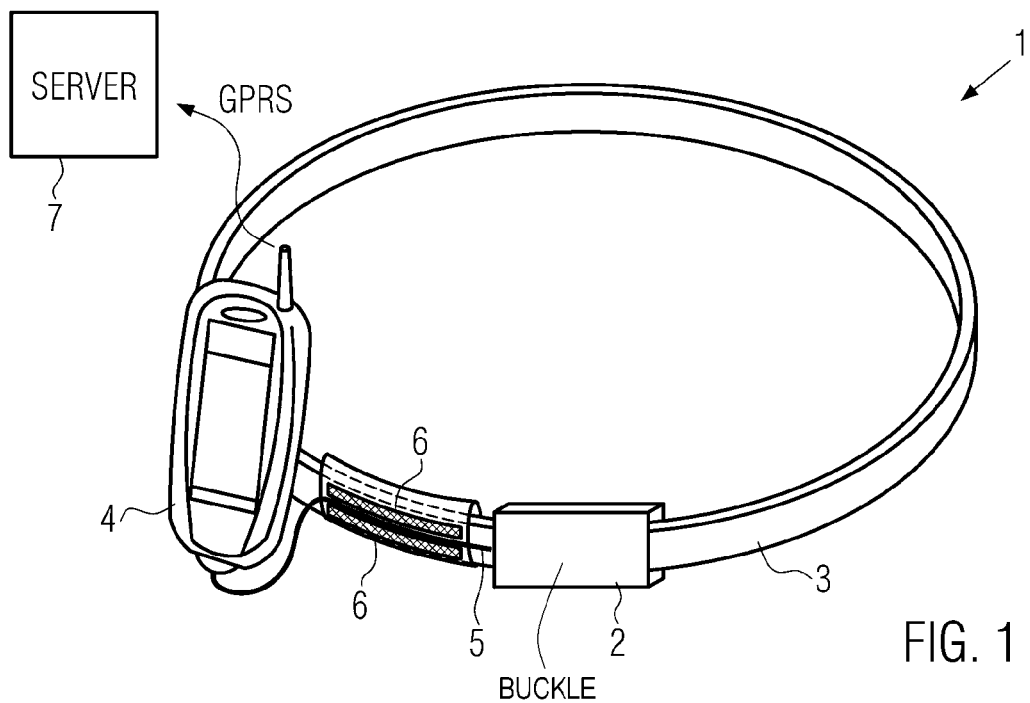
FIG. 1 a belt for attachment to the body of a patient, viewed from above, where the belt can be placed around the patient's waist and has a belt buckle with an activity measuring device incorporated therein, which is connected by a signal link to a mobile telephone that can be attached to the belt.

In FIG. 1 the activity measuring device 1 according to the invention is located in a belt buckle 2 of a belt 3 which can preferably be fitted around the patient's waist. Near the belt buckle 2, with the activity measuring device 1 incorporated therein, is an area of the belt with a case to hold a mobile telephone 4, which can also be configured as a PDA ("personal digital assistant"). Measurement data recorded by the activity measuring device 1 can be transmitted to the mobile telephone 4 via a connecting cable 5, which is electrically connected at one end to the activity measuring device 1 and at the other end to a device interface of the mobile telephone or PDA 4. At the same time the multi-wire connecting cable 5 is also electrically connected to the internal voltage supply unit of the PDA 4, and thus serves additionally as the power supply for the activity measuring device 1. The connecting cable 5 runs between the belt buckle 2 and the area of the belt to which the mobile telephone 4 is attached, and the belt 3 has on its surface a Velcro fastening 6, which serves to guide or secure the connecting cable 5 and has for this purpose a sealing joint running in the direction of longitudinal extension of the belt, so that the connecting cable can be inserted into the Velcro fastening when the sealing joint is open and is enclosed in sleeve form in the Velcro fastening when the sealing joint is then closed.

The measured acceleration data recorded by the device are transmitted via the connecting cable 5 to the mobile telephone, or to the PDA 4, and are sent from the mobile telephone 4 via a mobile radio network to an external server 7 for evaluation. This server 7 can be provided in a medical service centre, so that the data sent from the activity measuring device 1 can be retrieved by the medical staff at any time via an evaluation program implemented in the server 7.

Figure 2:
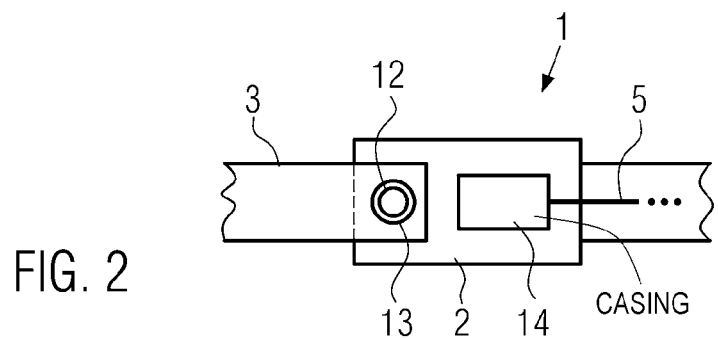
FIG. 2 a view of part of the belt from behind, in the area of the belt buckle, where the activity measuring device is integrated as a box in the belt buckle.

The activity measuring device 1 incorporated in the belt buckle 2 is represented in FIG. 2. The belt buckle 2 is a plane element made of metal or plastic, which is essentially planar or flat, and rectangular in the embodiment example. The activity measuring device 1 is arranged as a box or casing 14 on the back or inside of the belt buckle 2. The connecting cable 5 to the PDA 4 is brought out of the box 14 and extends along the outer surface (FIG. 1) of the adjoining area of the belt 3. At the opposite end of the belt buckle 2 there is a spur 12 on which the free end of the belt 3 can be fastened, by means of one or more holes 13 provided there (for adjustment of the circumference of the belt), in order to close the belt 3.

Figure 3:
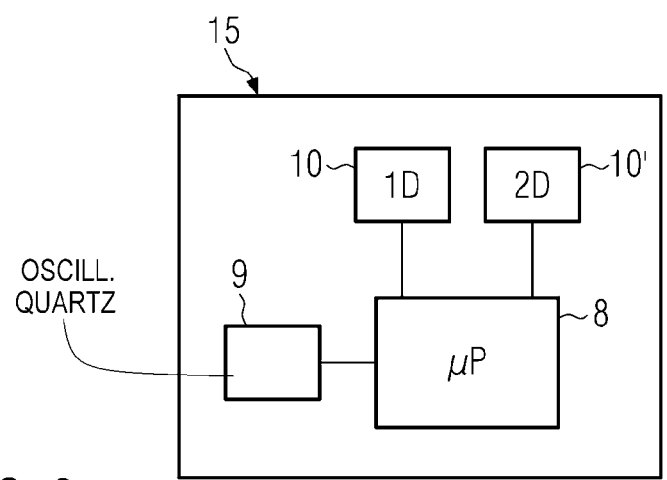
FIG. 3 a block diagram of a circuit, incorporated in the box of the activity measuring device according to the invention, which has a microprocessor, an oscillator quartz, for generating the processor clock rate of the microprocessor, and a unidimensional and a bidimensional accelerator sensor, for recording acceleration forces.

FIG. 3 shows a block diagram of a circuit 15 provided in the box 14 of the activity measuring device 1 according to the invention, where in the embodiment example a microprocessor or microcontroller 8, the processor clock rate of which is generated by an oscillator quartz 9, is linked by an active electrical connection to a unidimensionally and a bidimensionally operating acceleration sensor 10, 10' and records and processes the acceleration forces continuously measured by these acceleration sensors 10, 10' on the body of the patient to be examined, in all three spatial dimensions. In order to facilitate the calibration of the acceleration sensors 10, 10', the belt is fitted to the patient's body in such a way that the belt buckle, with the device 1 incorporated therein, is in contact with the body, so that one measurement axis of the bidimensionally operating acceleration sensor 10' virtually matches the direction of forward movement of the body. The acceleration sensors 10, 10' are arranged and connected in such a way that the unidimensionally operating sensor 10 measures acceleration forces acting along the vertical and the bidimensionally operating sensor 10' measures the acceleration forces acting at right angles thereto along both the remaining spatial axes of a Cartesian coordinate system. In this process the measured acceleration values x recorded in analogue form by the acceleration sensors 10, 10' are digitised via AD converters and converted into an interval $0 \leq x \leq 255$, where this interval corresponds for example to a measurement range from (−2g) to (+2g) and g is the gravitational acceleration, so that a digitised measurement value x from the interval $0 \leq x \leq 255$ can be converted in accordance with $(4/256)*x*g-2g$ into units of the gravitational acceleration g. A program implemented in a memory area of the microprocessor or microcontroller 8, as the case may be, controls on the one hand the recording of measurement values, and thus the interaction between the acceleration sensors 10, 10', the AD converters and the microprocessor 8—with a timer of the microprocessor 8, which is dependent on the processor clock rate, controlling the application and length of the measurement cycles—and on the other hand the processing of the measurement data in the microprocessor 8 and also the transmission thereof via an interface of the microprocessor 8 to the PDA 4. The measurement data recorded are stamped with the time and date, and in this way the patient's activity over the whole course of the day can be recorded.

Figure 4:
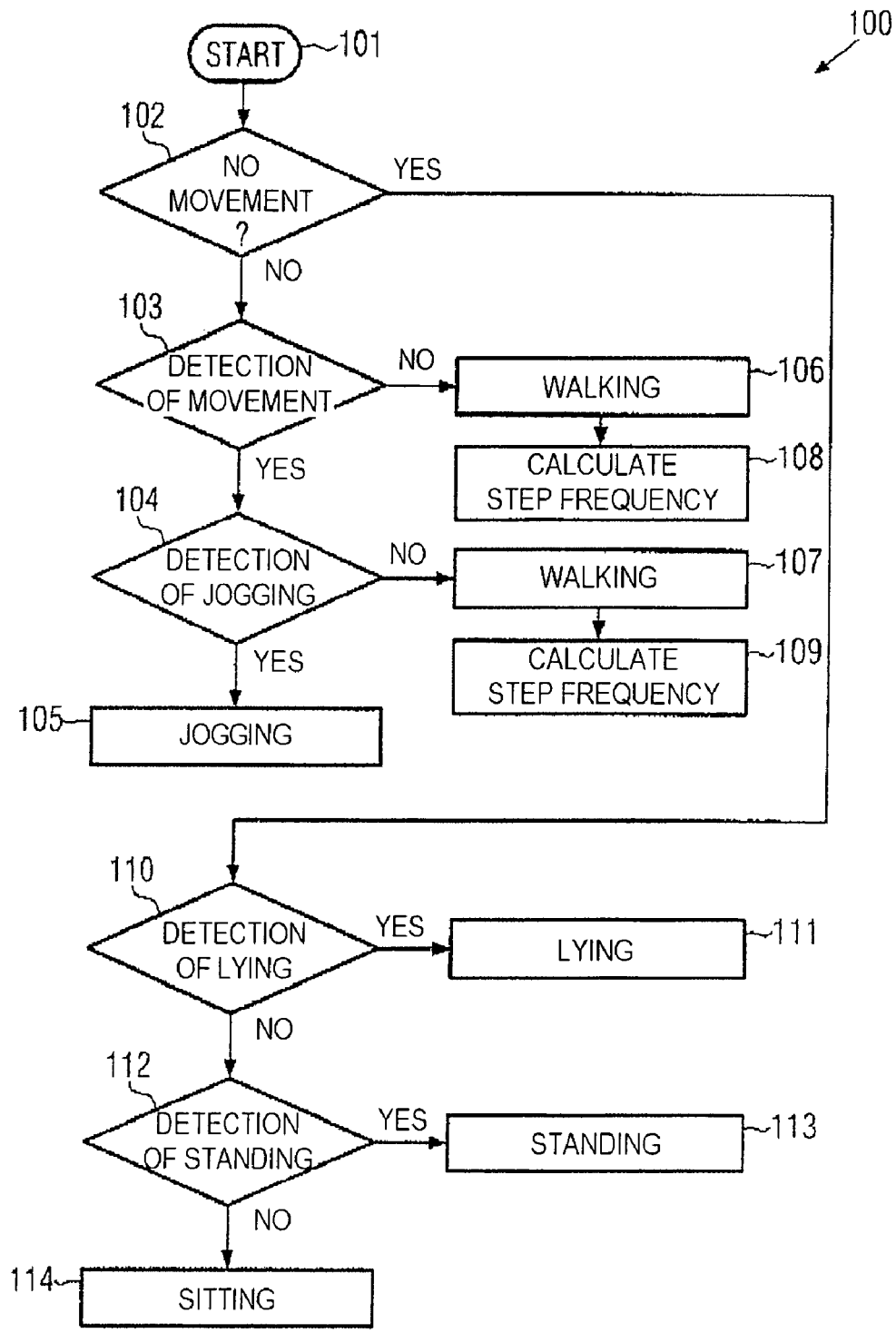
FIG. 4 a flowchart showing the main steps of the process occurring in the external server, or in the activity measuring device, for determination of the patient's current state of motion.

The essential steps of the method according to the invention are illustrated in FIG. 4 in a flowchart which as a whole is designated 100. After the start of the program 101 the step 102 first checks whether the criteria for no movement of the patient to be examined are fulfilled. To this end the maxima and minima of the accelerations for each spatial direction per second are calculated on the basis of the measurement data determined. The difference between the maxima and the minima is in each case compared with a specific threshold value δ in the direction of the y axis and in the direction of the z axis:

$$Max\_y-Min\_y \leq \delta \quad (1a)$$

or $$Max\_z-Min\_z \leq \delta \quad (1b),$$

where Max_y, Max_z are the maxima and the maxima means respectively of the acceleration values measured in the direction of the y axis and Min_y, Min_z are the minima and minima means respectively in the direction of the z axis, and δ is an empirically determined threshold value, the value of which is 20, where the digital value δ=20 in accordance with (4/256)*δ*g-2g can be converted into a corresponding g value. If one of the above two inequalities is fulfilled, the existence of no movement is classified as the degree of activity of the patient, and in subsequent steps of the process the program checks whether this immobility can be distinguished as lying, standing or sitting.

If the check in step 102 shows that the criteria for no movement are not fulfilled, the next step 103 of the method checks whether a movement of the patient can be detected on the basis of the following criteria:

$$Max\_y-Min\_y > \delta \quad (2a)$$

or $$Max\_z-Min\_z > \delta \quad (2b).$$

If therefore the difference between maximum and minimum in the direction of the y axis or in the direction of the z axis exceeds the threshold value δ=20, the criteria are fulfilled and a movement is detected.

In this case the program goes to step 104 and checks whether the person is jogging, by applying the following criteria for jogging to the measurement data determined:

$$MW\_Diff\_MWx < \gamma 1 \quad (3a)$$

and $$MW\_Diff\_MWy > \gamma 2 \quad (3b)$$

and $$MW\_Diff\_MWz < \gamma 3 \quad (3c),$$

where MW_Diff_MWx, MW_Diff_MWy, MW-Diff_MWz are in each case the differences determined from the mean of the accelerations in the relevant axis direction x, y, z and the values γ1=20, γ2=28, γ3=21 to be compared therewith are the relevant threshold values which as digital values in accordance with (4/256)*δ*g-2g can in each case be converted into a corresponding g value. In so doing, the mean differences of the measurement values $a_i$ from the mean are determined for 100 measurement values in accordance with the following equation:

$$\frac{1}{100}\sum_{i=1}^{100} |a_i - \text{Mean}| \quad (3d)$$

If each of the above inequalities (3a) to (3c) is fulfilled, the state of motion 105 of jogging is detected as the degree of activity. If the criteria checked in steps 103 and 104 of the method are not fulfilled, however, the program classifies the state of motion 106, 107 of walking and calculates a step frequency from the measurement data in corresponding computation steps 108, 109.

Following step 102 of the method, if the criteria applied in Eq. (1a) or (1b) are fulfilled, the program goes to step 110 of the method and checks whether the immobility is a recumbent state, by checking the corresponding criteria:

$$MW\_z > \alpha 11 \text{ and } MW\_y < \alpha 12 \quad (4a),$$

$$MW\_z < \alpha 21 \text{ and } MW\_y < \alpha 22 \quad (4b),$$

$$MW\_x < \alpha 31 \text{ and } MW\_y < \alpha 32 \quad (4c),$$

$$MW\_x > \alpha 41 \text{ and } MW\_y < \alpha 42 \quad (4d),$$

where MW_x, MW_y, MW_z are the relevant means of the measurement data in the direction of the x axis, direction of the y axis and direction of the z axis and are compared with the correspondingly assigned threshold values α11=47, α12=42, α21=-47, α22=12, α31=-43, α32=12, α41=43, α42=12. If inequality (4a) is fulfilled, the person examined is lying in a supine position; if inequality (4b) is fulfilled, the person is in a prone position; if inequality (4c) is fulfilled, the person is lying on their left side; and if inequality (4d) is fulfilled, the person is lying on their right side. In these four cases (4a) to (4d) the program detects the static state of motion or resting state 111 of recumbence.

If the check in that step of the method leads to a negative result, however, the program goes to step 112 of the method, which checks whether the person is standing up. To this end the following combination of inequalities is checked $$MW\_z < \beta 1 \text{ and } MW\_y - MW\_z \geq \beta 2 \quad (5).$$

If this combination of inequalities is fulfilled for the threshold values β1=2 and β2=-68 from the interval 0≤x≤255, the person is in the static state of motion 113 of standing. If the result of step 112 of the method is negative, the program classifies the static state of motion 114 of sitting.

For each form of motion identified, on the basis of the step frequency and duration of the form of motion identified, the program calculates a degree of activity which depends on physical parameters, namely the patient's height and weight, and on the energy requirement that is characteristic of the form of motion. A total degree of activity, which corresponds to the mean of the individual degrees of activity, weighted with the respective durations of motion, is also calculated for the entire duration of the measurement.

In addition, in the case of the form of motion of walking, it is possible to detect a limp or a stumble with the device according to the invention and the method according to the invention, on the basis of the tridimensional recording of the acceleration forces, by comparing the respective step durations for the left-sided and right-sided motion components of walking with each other and determining an asymmetry factor therefrom which indicates the existence of a limp or a stumble if a specific threshold value is exceeded.

The invention was explained in detail above on the basis of preferred embodiments thereof. It is obvious to a person skilled in the art, however, that different adaptations and modifications can be made without departing from the idea which underlies the invention.

The invention claimed is:

1. An activity measuring device for recording the activity of a test subject, wherein the activity measuring device is securable to a buckle of a belt that is configured to be fitted to the body of the test subject such that the activity measuring device can be carried on the body of the test subject, the activity measuring device includes at least one acceleration sensor configured to detect acceleration in all three spatial directions at right angles to each other, and the activity measuring device is configured to distinguish between states of motion of lying, standing and sitting associated with the test subject for each spatial axis direction by determining a mean for each spatial axis direction from a corresponding series of measurements determined for each spatial axis direction, and by further comparing each mean with a corresponding assigned threshold value for each spatial direction.

2. The activity measuring device according to claim 1, wherein the activity measuring device is securable to the belt buckle such that the activity measuring device is attachable close to the center of gravity of the test subject's body.

3. The activity measuring device according to claim 1, wherein the activity measuring device telemeters the recorded measurement data via a radio link to a central server.

4. The activity measuring device according to claim 3, wherein the activity measuring device is configured to be connected electrically to a mobile telephone that is securable to the belt so as to facilitate data transmission between the activity measuring device and the mobile telephone.

5. The activity measuring device according to claim 4, wherein the activity measuring device includes an electrical cable that is configured to be electrically connected to a device interface of the mobile telephone.

6. The activity measuring device according to claim 5, wherein a section of the belt adjoining the belt buckle on a side including the electrical cable side includes a Velcro fastener to receive the electrical cable.

7. The activity measuring device according to claim 4, wherein the measurement data recorded by the activity measuring device is transmitted to the mobile telephone via a device interface of the mobile telephone, and the measurement data is sent from the mobile telephone to the central server via the radio link.

8. The activity measuring device according to claim 1, wherein the at least one acceleration sensor of the activity measuring device comprises a unidimensionally operating acceleration sensor that records acceleration forces acting along a vertical spatial direction, and a bidimensionally operating acceleration sensor that records acceleration forces acting at right angles to the vertical spatial direction.

9. The activity measuring device according to claim 1, wherein the activity measuring device includes a microprocessor configured to control the recording of measurement data and data transmission.

10. The activity measuring device according to claim 1, wherein the activity measuring device records and transmits measurement data with a sampling frequency in an order of magnitude of 100 Hz.

11. A system comprising the activity measuring device of claim 1, a belt, and a mobile telephone.

12. The activity measuring device of claim 1, wherein the activity measuring device is configured to be secured to at least one of a front surface of the belt buckle, a back surface of the belt buckle, a side surface of the belt buckle, a top surface of the belt buckle and a bottom surface of the belt buckle.

13. The activity measuring device of claim 1, wherein the activity measuring device is configured to be secured within the belt buckle.

14. A method for recording an activity of a test subject, the method comprising:

continuously measuring, in three spatial directions that are at right angles to each other, body accelerations underlying the momentary physical activity of the test subject; and determining a current state of motion based upon the continuous measurements of the body accelerations of the test subject;

wherein, in order to distinguish states of motion of walking and jogging associated with the test subject, a mean difference from a mean of measured values in a series of measurements is determined for each spatial axis direction, and the mean difference determined for each spatial axis direction is compared with a corresponding threshold value assigned to each spatial axis direction.

15. The method according to claim 14, wherein a distinction is made between static and dynamic states of motion.

16. The method according to claim 15, wherein a distinction is made between sitting, standing and lying for static states of motion of the test subject, and between walking and jogging for dynamic states of motion of the test subject.

17. The method according to claim 15, wherein, in order to distinguish between static and dynamic states of motion, a maximum and a minimum in a series of consecutively measured acceleration values determined in the direction of one spatial axis are calculated and the difference between the maximum and the minimum is compared with a threshold value.

18. The method according to claim 14, wherein a movement of the test subject is detected when the inequality max−min>$\delta$ is fulfilled in at least one spatial axis direction, where max and min are respectively maximum and minimum values calculated from a series of consecutively measured acceleration values determined in the at least one spatial axis direction, and $\delta$ is a threshold value.

19. A method for recording an activity of a test subject, the method comprising:

continuously measuring, in three spatial directions that are at right angles to each other, body accelerations underlying the momentary physical activity of the test subject; and determining a current state of motion based upon the continuous measurements of the body accelerations of the test subject;

wherein, in order to distinguish states of motion of lying, standing and sitting associated with the test subject for each spatial axis direction, a mean is determined for each spatial axis direction from corresponding series of measurements determined for each spatial axis direction, and each mean is compared with a corresponding assigned threshold value for each spatial direction.

20. An activity measuring device for recording the activity of a test subject, wherein the activity measuring device is securable to a buckle of a belt that is configured to be fitted to the body of the test subject such that the activity measuring device can be carried on the body of the test subject, the activity measuring device includes at least one acceleration sensor configured to detect acceleration in all three spatial directions at right angles to each other, and the activity measuring device is configured to distinguish between states of motion of walking and jogging associated with the test subject by determining a mean difference from a mean of measured values in a series of measurements for each spatial axis direction, and by further comparing the mean difference determined for each spatial axis direction with a corresponding threshold value assigned to each spatial axis direction.

* * * * *